United States Patent
Björk et al.

(10) Patent No.: US 11,717,500 B2
(45) Date of Patent: Aug. 8, 2023

(54) TREATMENT OF SPONDYLOARTHRITIS

(71) Applicant: PHARMACYL AB, Bjärred (SE)

(72) Inventors: Anders Björk, Bjärred (SE); Gunnar Hedlund, Lund (SE)

(73) Assignee: PHARMACYL AB, Bjarred (SE)

( * ) Notice: Subject to any disclaimer, the term of this patent is extended or adjusted under 35 U.S.C. 154(b) by 87 days.

(21) Appl. No.: 17/158,117

(22) Filed: Jan. 26, 2021

(65) Prior Publication Data

US 2021/0236441 A1 Aug. 5, 2021

(30) Foreign Application Priority Data

Feb. 3, 2020 (EP) .................... 20155130

(51) Int. Cl.
*A61K 31/167* (2006.01)
*A61P 19/02* (2006.01)

(52) U.S. Cl.
CPC ............ *A61K 31/167* (2013.01); *A61P 19/02* (2018.01)

(58) Field of Classification Search
CPC .................................................. A61K 31/167
See application file for complete search history.

(56) References Cited

U.S. PATENT DOCUMENTS

| | | | |
|---|---|---|---|
| 3,177,252 A | 4/1965 | Thominet | |
| 6,518,312 B2 | 2/2003 | Bjork et al. | |
| 2011/0027179 A1 | 2/2011 | Friebe et al. | |

FOREIGN PATENT DOCUMENTS

| | | | | |
|---|---|---|---|---|
| WO | 9963987 A1 | 12/1999 | | |
| WO | 2005025498 A2 | 3/2005 | | |
| WO | 2014064229 A1 | 5/2014 | | |
| WO | 2020035554 A1 | 2/2020 | | |
| WO | 2020035555 A2 | 2/2020 | | |
| WO | WO2020/035554 | * | 2/2020 | ........... A61K 31/166 |
| WO | WO2020/035555 | * | 2/2020 | ........... A61K 31/166 |

OTHER PUBLICATIONS

Extended European Search Report for corresponding European Application EP20155130.6 dated Jul. 31, 2020.
Liberg D et al., "N-substituted benzamides inhibit NFkB activation and induce apoptosis by separate mechanisms", Br J Cancer. 1999 81:981-8.
Lindgren H et al., "N-substituted benzamides inhibit nuclear factor-kB and nuclear factor of activated T cells while inducing activator protein 1 activity in T lymphocytes", Mol Immunol. 2001 38:267-77.
Lindgren H et al., "Differential usage of IκBα and IκBβ in regulation of apoptosis versus gene expression", Biochem Biophys Res Commun. 2003 301:204-11.
Thompson JE et al., "IκBβ Regulates the Persistent Response in a Biphasic Activation of NF-κB", Cell. 1995 80:573-82.

* cited by examiner

*Primary Examiner* — Paul V Ward
(74) *Attorney, Agent, or Firm* — Renner, Otto, Boisselle & Sklar, LLP

(57) ABSTRACT

A method for the treatment a disease resulting from spondyloarthritis, such as axial spondyloarthritis, psoriatic arthritis and enteropathic arthritis, by administering, to a mammal in need of such treatment, a compound of formula (I)

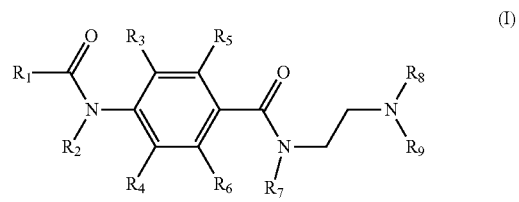

or a pharmaceutically acceptable salt or solvate thereof.

17 Claims, No Drawings

TREATMENT OF SPONDYLOARTHRITIS

FIELD OF THE INVENTION

The present invention relates to methods for the treatment of diseases resulting from spondyloarthritis. More particularly, the invention relates to methods for the treatment of diseases resulting from axial spondyloarthritis, psoriatic arthritis and enteropathic arthritis by administration of 4-alkanoylaminobenzamide derivatives. Furthermore, the invention relates to combinations and pharmaceutical formulations comprising such compounds.

BACKGROUND OF THE INVENTION

Throughout this application, various (non-patent) publications are referred to by first author and year of publication. Full citations for these publications are presented in a References section immediately before the claims. The disclosures of these documents and publications referred to herein are hereby incorporated in their entireties by reference into this application in order to more fully describe the state of the art to which this invention pertains.

Spondyloarthritis (SpA) is a type of arthritis that attacks the spine (axial SpA) and, in some people, the joints of the arms and legs (peripheral SpA). SpA is an umbrella term applied to a group of rheumatic diseases with features in common with but also distinct from other inflammatory arthritides, particularly rheumatoid arthritis (RA). The various forms of SpA include ankylosing spondylitis (AS), psoriatic arthritis (PsA), enteropathic arthritis (EnA), reactive arthritis, juvenile SpA, and undifferentiated SpA.

Axial SpA, comprised of AS and nonradiographic axial SpA (nr-axSpA), is the main form of chronic inflammatory arthritis affecting the axial skeleton. Nr-axSpA shares several features with AS but is characterized by lack of spine ankylosis. AS, affecting 0.1-0.5% of the population, is characterized by inflammatory back pain, radiographic sacroiliitis, and excess spinal bone formation and can impose substantial physical and social burdens on patients. Skeletal disease may be accompanied by uveitis, psoriasis, and inflammatory bowel disease (IBD). Arthritis is the most common extraintestinal manifestation of IBD and can have a significant impact on morbidity and quality of life. It has been suggested that clinically silent macroscopic and microscopic gut inflammation occurs in about 60% of AS patients.

Current treatment guidelines of AS and nr-axSpA recommend anti-TNF agents as a treatment option on inadequate response following treatment with non-steroidal anti-inflammatory drugs (NSAIDs). An insufficient response to NSAID therapy is identified as active disease despite the administration of at least two different NSAIDs at the maximum anti-inflammatory dose. For localized joint swelling, injections of corticosteroid medications into joints or tendon sheaths can be effective. Corticosteroids taken by mouth are not advised because of many side effects. Biologic treatment is not without side effects, including an increased risk for serious chronic infections, in particular affecting the respiratory tract. Moreover, anti-TNF blockers cannot maintain long-term remission. When patients fail to respond to the first TNF-α blocker, treatment with a second biologic is advised. The different biologic can be an interleukin-17A (IL-17A) inhibitor. The goals of treatment are to alleviate symptoms, improve functioning, and decrease disease complications as much as possible.

Psoriatic arthritis (PsA) has been defined as a unique inflammatory arthritis associated with psoriasis. PsA is a heterogeneous condition with different clinical phenotypes, varying in severity, disease course and numbers of affected joints. Diagnostic criteria for PsA have not been validated, but the CASPAR criteria provide guidance to clinicians. PsA is a chronic inflammatory disorder and patients with PsA can experience substantial disability, with severe joint damage, digital deformation, functional impairment, and impairment of quality of life. Its exact prevalence is unknown but estimates vary from 0.3% to 1% of the population.

Current treatment guidelines recommend biologic disease-modifying antirheumatic drugs (DMARDs) as a treatment option on inadequate response following treatment with non-steroidal anti-inflammatory drugs (NSAIDs), corticosteroids and conventional synthetic DMARDs. Despite the advent of therapeutics targeting tumour necrosis factor (TNF), IL-17A, or IL-12/23, an unmet need remains in PsA as a significant proportion of patients either do not respond or eventually lose response to currently available therapies.

Enteropathic arthritis (EnA) refers to acute or subacute arthritis in association with, or as a reaction to, a usually colonic inflammatory condition (ulcerative colitis and Crohn's disease). Individuals with EnA may have inflammatory arthritis in one or more peripheral (limb) joints such as an arm or leg, although the lower limbs are more commonly affected. The severity of the peripheral arthritis normally coincides with the severity of the IBD. Individuals with IBD also has spinal inflammation, although this is independent of the severity of the bowel disease symptoms. The spinal inflammation may just be arthritis in the sacroiliac joints, but the entire spine may be involved.

In EnA medications may need to be adjusted so the gastrointestinal component of the disease is also treated and not exacerbated.

As noted herein above, some patients suffering from SpA do not respond to conventional treatment, or respond poorly to such treatment and, for such patients other modes of treatment must be provided.

Some 4-alkanoylaminobenzamides (hereinafter AABZ) have been previously described, with or without indication of a particular use. Thus, US Patent Application No. 2011/0027179 discloses 4-acetamido-N-[2-(diethylamino)ethyl]-2-methoxybenzamide, N-[2-(diethylamino)ethyl]-2-methoxy-4-(propanoylamino)benzamide, N-[2-[di(propan-2-yl)amino]ethyl]-2-ethoxy-4-(propanoylamino)-benzamide, N-[2-(diethylamino)ethyl]-2-ethoxy-4-(propanoylamino)benzamide, 4-propionylamino-N-(2-diisopropylamino-ethyl)-2-ethoxy-benzamide, 4-propionylamino-N-(2-dibutylamino-ethyl)-2-ethoxy-benzamide. US Patent Application No. 2011/0027179, however, is directed to radiohalogenated benzamide derivatives and their use in tumour diagnosis and tumour therapy, which means that the disclosed compounds supposedly are used as synthesis intermediates.

WO 2014/064229 discloses the use the AABZs to enhance the protective immunity elicited by an immunogen. Mention is made of 4-acetamido-3-chloro-N-[2-(diethylamino)ethyl]benzamide, 4-acetamido-5-chloro-N-[2-(diethylamino)ethyl]-2-methoxybenzamide, and 4-acetamido-N-[2-(diethylamino)ethyl]benzamide.

WO 2005/025498 indicates that some AABZs, when delivered topically, cause cellular (eosinophil) apoptosis and based on this effect, discloses the use of such compounds for the treatment of acute or chronic respiratory tract inflammation associated with eosinophil infiltration. Mention is made of 4-acetamido-N-[2-(diethylamino)ethyl]benzamide and N-[2-(diethylamino)ethyl]-4-(pentanoylamino)benzamide.

U.S. Pat. No. 3,177,252 discloses compounds of a generic formula that includes AABZ, for the treatment of emesis, and behaviour disturbances, without however mentioning any example of an AABZ.

Acecainide (4-acetamido-N-[2-(diethylamino)ethyl]benzamide; CAS No. 32795-44-1) has been used for the treatment or prevention of cardiac arrhythmias.

The invention disclosed in WO 99/63987 embraces 4-acetamido-3-chloro-N-[2-(diethylamino)ethyl]benzamide (N-acetyldeclopramide; hereinafter Cpd A) and uses thereof for inhibiting or killing tumour or cancer cells and as a potential therapeutic agents for treating of inflammatory disorders, such as systemic lupus erythematosus rheumatoid arthritis, ulcerative colitis and psoriasis. WO 2020/035554 A1 and WO 2020/035555 A2 disclose Cpd A and other examples of AABZs for the treatment of IBD.

Cpd A has been shown to be non-apoptotic and to inhibit activities of NF-κB and NFAT and to induce AP-1 activity in T cells (Liberg D, 1999; Lindgren H, 2001; Lindgren H, 2003). Furthermore, Cpd A has been found to inhibit breakdown of IκBβ (Liberg D, 1999; Lindgren H, 2001).

SUMMARY OF THE INVENTION

A primary objective of the present invention is to provide a new method for the treatment of SpA. The present inventors contemplate that a more effective treatment of SpA than today's may necessitate drugs with a new mode of action. The AABZs have a new and unique mode of action. They have been shown to inhibit activation of the NF-κB by selectively inhibiting IκBβ breakdown. NF-κB is a central transcription regulatory factor involved in mediating the initiation and perpetuation of inflammatory processes. NF-κB is sequestered in the cytoplasm of mammalian cells as inactive complexes bound to inhibitory molecules known as inhibitors of κB (IκB), preventing free NF-κB from entering the cell nucleus. Cell activation with different inducers results in the degradation of the inactive complexes and translocation of free NF-kB to the cell nucleus, with resultant induction of NF-κB activity. Inhibition of IκB breakdown inhibits induction of NF-κB activity, leading to suppressed expression of genes for inflammatory mediators.

There are two major forms of IκB proteins, IκBα and IκBβ. One class of inducers causes rapid but transient activation of NF-κB mediated through IκBa, whereas another class of inducers causes persistent long-term activation of NF-κB mediated through IκBβ (Thompson J E, 1995). AABZs have been shown to inhibit activation of NF-κB by selectively inhibiting IκBβ breakdown. Without wishing to be bound to any theory, blocking IκBβ may represent a powerful and promising new strategy for selectively inhibiting the chronic phase of TNFα production, and by that the AABZs open for successful treatment of chronic inflammatory diseases such as SpA.

Thus, a first aspect is a method for the treatment of a disease resulting from SpA, comprising administering, to a mammal in need of such treatment, a therapeutically effective amount of a compound of formula (I)

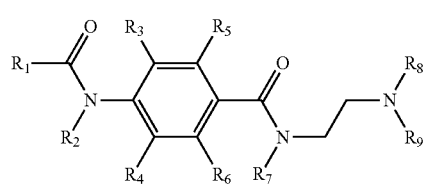

(I)

or a pharmaceutically acceptable salt or solvate thereof; wherein $R_1$ is selected from C1-C6 alkyl and C3-C6 cycloalkyl;
$R_2$ is selected from hydrogen and C1-C3 alkyl;
$R_3$, $R_4$, $R_5$, and $R_6$ are independently selected from hydrogen, C1-C3 alkyl, C1-C3 alkoxy, C1-C3 alkylthio, fluoro, chloro, and bromo, wherein any alkyl is optionally substituted with one or more fluoro;
$R_7$ is selected from hydrogen and C1-C3 alkyl; and
$R_8$ and $R_9$ are independently selected from C1-C6 alkyl.

In some embodiments, the mammal is one for which NSAID, DMARD and anti-TNF-α treatment is not useful.

In some embodiments, the mammal is one for which NSAID or anti-TNF-α treatment is not useful.

In some embodiments, the mammal is one for which anti-TNF-α treatment is not useful.

In some embodiments, the mammal is one for which NSAID treatment is not useful.

In some embodiments, the mammal is one for which DMARD treatment is not useful.

A further aspect is a pharmaceutical composition comprising a combination of a compound of formula (I) as defined herein, and a further therapeutically active ingredient, and optionally a pharmaceutically acceptable excipient for use in the treatment of a disease resulting from SpA.

A further aspect is a kit-of-parts for use in the treatment of a disease resulting from SpA, comprising a combination of a compound of formula (I) as defined herein above or a pharmaceutically acceptable salt or solvate thereof, and (ii) a further therapeutically active ingredient, wherein each one of components (i) and (ii) is optionally formulated in admixture with a pharmaceutically acceptable excipient.

Other features and advantages of the invention will be understood by references to the detailed description and examples that follow.

DETAILED DESCRIPTION OF THE INVENTION

Definitions

As used herein, and unless stated otherwise and unless otherwise apparent from the context, each of the following terms shall have the definition set forth below.

The term "Cn alkyl" refers to a linear or branched chain saturated hydrocarbyl radical containing n carbon atoms in the chain, i.e. a moiety of formula $C_nH_{2n+1}$.

The term "Cn-Cm alkyl" refers to a linear or branched chain alkyl radical containing a number of carbon atoms in the chain ranging from n to m, wherein n and m are both integers and m is higher than n.

The term "Cn cycloalkyl" refers to a cyclic hydrocarbyl radical of formula $C_nH_{2n-1}$.

The term "Cn-Cm cycloalkyl" refers to a cyclic hydrocarbyl radical containing a number of carbon atoms in the cycle ranging from n to m, wherein n and m are both integers and m is higher than n.

The term "Cn-Cm alkoxy" refers to a moiety of formula

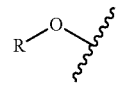

wherein R is Cn-Cm alkyl. For example, methoxy is C1 alkoxy.

The term "Cn-Cm alkylthio" refers to a moiety of formula

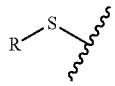

wherein R is Cn-Cm alkyl. For example, methylthio is C1 alkylthio.

The term "halogen" refers to F, Cl, Br or I; preferably F, Cl or Br.

The term "hydroxy" refers to the moiety

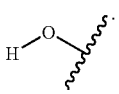

As used herein, "AABZ" means a compound of formula (I) as described herein, unless otherwise indicated or apparent from the context. Furthermore, unless otherwise indicated or apparent from the context, the term also includes a pharmaceutically acceptable salt or solvate (including hydrate) thereof.

As used herein, "about" in the context of a numerical value or range means ±20% of the numerical value or range recited or claimed.

As used herein, "administration", "administering" etc. means the giving of, dispensing of, or application of medicines, drugs, or remedies to a subject (e.g. a mammal subject, preferably a human) to relieve or cure a pathological condition. Oral administration is one way of administering the instant compounds to the subject.

As used herein, an "amount" or "dose" of a compound (e.g. AABZ) as measured in milligrams refers to the milligrams of the compound present in a preparation, regardless of the form of the preparation. A "dose of 5.0 mg of a compound" means the amount of compound in a preparation is 5.0 mg, regardless of the form of the preparation. Thus, when in the form of a salt, e.g. a hydrochloride, the weight of the salt form necessary to provide a dose of 5.0 mg of the free base compound would be greater than 5.0 mg due to the presence of the additional acid.

As used herein, "anti-TNF-α treatment" refers to treatment aiming to reduce TNF-α activity and/or TNF-α production, normally for a therapeutic purpose, such as for the treatment of an inflammatory disorder.

As used herein, "AP-1" means activator protein-1.

As used herein, "AS" means ankylosing spondylitis.

As used herein "axSpA" means axial spondyloarthritis.

As used herein, "combination" means an assemblage of compounds for use in therapy either by simultaneous or separate (e.g. sequential or concomitant) administration. Simultaneous administration refers to administration of an admixture (whether a true mixture, a suspension, an emulsion or other physical combination) of two active ingredients (e.g. the AABZ and a further, therapeutically active agent). In this case, the combination may be an admixture of the AABZ and the further agent; or the AABZ and the further agent may be provided in separate containers and combined just prior to administration. Separate administration may be sequential (i.e. consecutive) or concomitant (i.e. happening at the same time).

Separate administration refers to the concomitant or sequential administration of the AABZ and the further therapeutically active agent as separate formulations, but at the same time or at times sufficiently close together for an activity to be observed that is at least additive, relative to the activity of either one of the AABZ and the further, therapeutically active agent alone.

As used herein "CASPAR" means Classification Criteria for Psoriatic Arthritis.

As used herein, "Cpd A" means 4-acetamido-3-chloro-N-[2-(diethylamino)ethyl]benzamide (N-acetyldeclopramide) hydrochloride.

As used herein DMARD means a disease-modifying antirheumatic drug.

As used herein, "effective" when referring to an amount of a therapeutically active agent, e.g. AABZ, refers to the amount that is sufficient to yield a desired therapeutic response without undue adverse side effects (such as toxicity, irritation, or allergic response), commensurate with a reasonable benefit/risk ratio when used in the manner of this invention.

As used herein "EnA" means enteropathic arthritis.

As used herein, "excipient" refers to a substance formulated alongside the active ingredient of a medication included for such purposes as long-term stabilization, to provide bulk to a solid formulation, to act as a carrier and/or diluent, to confer a therapeutic enhancement on the active ingredient in the final dosage form, e.g. by facilitating absorption, reducing viscosity, or enhancing solubility. An excipient can also be useful in the manufacturing process, e.g. by facilitating powder flowability or providing non-stick properties. Examples of excipients are antiadherents, binders, coatings, colours, disintegrants, flavours, glidants, lubricants, preservatives, sorbents, sweeteners, and vehicles (carriers).

As used herein "IκB" means inhibitor of kappa B.

As used herein "IL" means interleukin.

As used herein "inflammatory bowel disease" or "IBD" refers to diseases of the bowel associated with inflammation and/or ulceration and includes e.g. Crohn's disease and ulcerative colitis.

As used herein, "NFAT" means nuclear factor of activated T cell.

As used herein, "NFκB" means nuclear factor kappa B.

AS used herein "nr-axSpA" means nonradiographic axial SpA.

As used herein "NSAID" means non-steroid anti-inflammatory drug.

As used herein, "patient" or "subject" refers to a mammal patient or subject, selected from animals and humans, and the two terms may be interchangeably used.

As used herein, "pharmaceutically acceptable" refers to that which is suitable for use with humans and/or animals, generally safe and non-toxic at normal use, i.e. without undue adverse side effects (such as toxicity, irritation, and allergic response) commensurate with a reasonable benefit/risk ratio.

As used herein, "PsA" means psoriatic arthritis.

As used herein, a "salt thereof" is a salt of the instant compounds which have been modified by making acid or base salts of the compounds. The term "pharmaceutically acceptable salt" in this respect, refers to the relatively non-toxic, inorganic and organic acid or base addition salts of compounds of the present invention. For example, one means of preparing such a salt is by treating a compound of the present invention with an inorganic acid.

As used herein, a "solvate" means a physical association of a compound (e.g. a compound of formula (I)) with one or more solvent molecules, e.g. by hydrogen bonding. "Solvate" encompasses both solution-phase and isolable solvates. Exemplary solvates include, but are not limited to, hydrates, ethanolates, methanolates, and isopropanolates. Methods of solvation are generally known to the person of ordinary skill in the art.

As used herein, "SpA" means spondyloarthritis.

As used herein, a "subject afflicted with a disease resulting from SpA" means a subject who was been clinically diagnosed to have such a disease.

As used herein, a "symptom" associated with a disease resulting from SpA includes any clinical or laboratory manifestation associated with the disease and is not limited to what the subject can feel or observe.

As used herein, "TNF" means tumour necrosis factor.

As used herein, "TNF-α" means tumour necrosis factor alpha.

As used herein, "treating" encompasses, e.g., inducing inhibition, regression, or stasis of a disease or disorder, or alleviating, lessening, suppressing, inhibiting, reducing the severity of, eliminating, or substantially eliminating, or ameliorating a symptom of the disease or disorder.

As used herein, the expression "treatment that is not useful", refers to a treatment that either cannot be used for some reason (e.g. due to unacceptable secondary effects) or that does not give rise to a sufficient therapeutic effect.

The Compound of Formula (I)

In a compound of formula (I) as defined herein, $R_1$ is selected from C1-C6 alkyl and C3-C6 cycloalkyl.

In some embodiments, $R_1$ is selected from C1-C5 alkyl and C3-C5 cycloalkyl, e.g. from C1-C4 alkyl and C3-C4 cycloalkyl, or from C1-C3 alkyl and C3 cycloalkyl.

In some embodiments, $R_1$ is selected from C1-C6 alkyl, e.g. from C1-C5 alkyl or from C1-C4 alkyl or from C1-C3 alkyl, or from C1-C2 alkyl.

In some embodiments, $R_1$ is selected from methyl, ethyl, n-propyl, iso-propyl, cyclopropyl, n-butyl, sec-butyl, iso-butyl, tert-butyl, cyclobutyl, n-pentyl, sec-pentyl, iso-pentyl, tert-pentyl, neo-pentyl, and cyclopentyl; e.g. from methyl, ethyl, n-propyl, iso-propyl, cyclopropyl, n-butyl, sec-butyl, iso-butyl, tert-butyl, n-pentyl, sec-pentyl, iso-pentyl, tert-pentyl, and neo-pentyl.

In some embodiments, $R_1$ is selected from methyl, ethyl, n-propyl, iso-propyl, cyclopropyl, n-butyl, sec-butyl, iso-butyl, tert-butyl, and cyclobutyl, e.g. from methyl, ethyl, n-propyl, iso-propyl, cyclopropyl, n-butyl, sec-butyl, iso-butyl, and tert-butyl.

In some embodiments, $R_1$ is selected from methyl, ethyl, n-propyl, iso-propyl, and cyclopropyl, e.g. from methyl, ethyl, n-propyl, and iso-propyl.

In some embodiments, $R_1$ is selected from methyl, ethyl, n-propyl, iso-propyl, n-butyl, sec-butyl, iso-butyl, tert-butyl, n-pentyl, sec-pentyl, iso-pentyl, tert-pentyl, and neo-pentyl; e.g. from methyl, ethyl, n-propyl, iso-propyl, n-butyl, sec-butyl, iso-butyl, and tert-butyl; or from methyl, ethyl, n-propyl, and iso-propyl; e.g. from methyl, ethyl, and iso-propyl.

In some embodiments, $R_1$ is methyl or ethyl. In some embodiments, $R_1$ is methyl. In some embodiments, $R_1$ is ethyl. In some embodiments, $R_1$ is iso-propyl.

The moiety $R_2$ is selected from hydrogen and C1-C3 alkyl.

In some embodiments, $R_2$ is selected from hydrogen, methyl, ethyl, n-propyl and iso-propyl; e.g. from hydrogen, methyl and ethyl, or from hydrogen and methyl.

In some embodiments, $R_2$ is hydrogen.

The moieties $R_3$, $R_4$, $R_5$, and $R_6$ are independently selected from hydrogen, C1-C3 alkyl, C1-C3 alkoxy, C1-C3 alkylthio, fluoro, chloro, bromo, wherein any alkyl is optionally substituted with one or more fluoro.

In some embodiments, $R_3$, $R_4$, $R_5$, and $R_6$ are independently selected from hydrogen, C1-C3 alkyl, C1-C3 alkoxy, C1-C3 alkylthio, and fluoro, chloro, bromo, wherein any alkyl is optionally substituted with one or more fluoro.

In some embodiments, $R_3$, $R_4$, $R_5$, and $R_6$ are independently selected from hydrogen, C1-C3 alkyl, C1-C3 alkoxy, and fluoro, chloro, bromo, wherein any alkyl is optionally substituted with one or more fluoro. In still other embodiments, $R_3$, $R_4$, $R_5$, and $R_6$ are independently selected from hydrogen, C1-C3 alkyl and fluoro, chloro, bromo, wherein any alkyl is optionally substituted with one or more fluoro.

In still other embodiments, $R_3$, $R_4$, $R_5$, and $R_6$ are independently selected from hydrogen, C1-C3 alkoxy and fluoro, chloro, bromo, wherein any alkyl is optionally substituted with one or more fluoro. In still other embodiments, $R_3$, $R_4$, $R_5$, and $R_6$ are independently selected from hydrogen, C1-C3 alkoxy, C1-C3 alkylthio, and fluoro, chloro, bromo, wherein any alkyl is optionally substituted with one or more fluoro. In still further embodiments, $R_3$, $R_4$, $R_5$, and $R_6$ are independently selected from hydrogen and fluoro, chloro, bromo.

When any one of $R_3$, $R_4$, $R_5$, and $R_6$ is selected from C1-C3 alkyl, it e.g. may be selected from methyl and ethyl; in particular it may be methyl.

When any one of $R_3$, $R_4$, $R_5$, and $R_6$ is selected from C1-C3 alkoxy, it e.g. may be selected from methoxy and ethoxy; in particular it may be methoxy.

In some embodiments, $R_5$ and $R_6$ are not C1-C3 alkoxy.

When any one of $R_3$, $R_4$, $R_5$, and $R_6$ is selected from C1-C3 alkylthio, it e.g. may be selected from methylthio and ethylthio; in particular it may be methylthio.

In some embodiments, when any one of $R_3$, $R_4$, $R_5$, and $R_6$ is a halogen selected from fluoro, chloro and bromo, said halogen is selected from chloro and bromo, in particular it is chloro. In some further embodiments, when any one of $R_3$, $R_4$, $R_5$, and $R_6$ is a halogen selected from fluoro, chloro and bromo, said halogen is selected from fluoro and chloro.

In some embodiments, $R_3$, $R_4$, $R_5$, and $R_6$ are independently selected from hydrogen, methyl, ethyl, methoxy, ethoxy, methylthio, fluoro, chloro, bromo, and trifluoromethyl; e.g. from hydrogen, methyl, ethyl, methoxy, ethoxy, methylthio, fluoro, chloro, bromo, and trifluoromethyl; or from hydrogen, methyl, ethyl, methoxy, ethoxy, fluoro, chloro, bromo, and trifluoromethyl; e.g. from hydrogen, methyl, methoxy, fluoro, chloro, bromo, and trifluoromethyl; or from hydrogen, methyl, methoxy, chloro, and trifluoromethyl; or from hydrogen, methyl, methoxy and chloro; or from hydrogen, methoxy and chloro; or from hydrogen, methyl and chloro; e.g. from hydrogen and chloro.

In some of the above embodiments, at least one, more preferably at least two of $R_3$, $R_4$, $R_5$, and $R_6$ are hydrogen. In some of the above embodiments, two of $R_3$, $R_4$, $R_5$, and $R_6$ are hydrogen. In some of the above embodiments, three of $R_3$, $R_4$, $R_5$, and $R_6$ are hydrogen. In some of the above embodiments, each one of $R_3$, $R_4$, $R_5$, and $R_6$ is hydrogen. In some of the above embodiments, at least one of $R_3$, $R_4$, $R_5$, and $R_6$ is different from hydrogen. In some of the above embodiments, one of $R_3$, $R_4$, $R_5$, and $R_6$ is different from hydrogen and the three others are hydrogen; e.g. one of $R_3$, $R_4$, $R_5$, and $R_6$ (e.g. $R_3$) is halogen, such as chloro; and the three others are hydrogen. In some of the above embodiments, $R_3$ is different from hydrogen, and each one of $R_4$, $R_5$, and $R_6$ is hydrogen.

In some embodiments, $R_5$ is different from hydrogen, and each one of $R_3$, $R_4$, and $R_6$ is hydrogen.

In some embodiments, one of $R_3$, $R_4$, $R_5$, and $R_6$ (e.g. $R_3$) is fluoro, chloro, or bromo, in particular chloro; and the three others are hydrogen.

In some embodiments, $R_3$ is hydrogen or halogen, e.g. hydrogen or chloro; and $R_4$, $R_5$, and $R_6$ are hydrogen.

In some embodiments, $R_4$, and $R_6$ are hydrogen; e.g. $R_4$ and $R_6$ are hydrogen and at least one of $R_3$ and $R_5$ is different from hydrogen, e.g. both $R_3$ and $R_5$ are different from hydrogen.

In some embodiments, $R_4$ and $R_5$ are hydrogen; e.g. $R_4$ and $R_5$ are hydrogen and at least one of $R_3$ and $R_6$ is different from hydrogen, e.g. both $R_3$ and $R_6$ are different from hydrogen.

In some embodiments, $R_3$ and $R_4$ are hydrogen; e.g. $R_3$ and $R_4$ are hydrogen and at least one of $R_5$ and $R_6$ is different from hydrogen, e.g. both $R_5$ and $R_6$ are different from hydrogen. In some of the above embodiments, $R_5$ and $R_6$ are not methoxy or ethoxy.

The moiety $R_7$ is selected from hydrogen and C1-C3 alkyl.

In some embodiments, $R_7$ is selected from hydrogen, methyl, ethyl, propyl and iso-propyl; e.g. from hydrogen, methyl, ethyl, and propyl.

In some embodiments, $R_7$ is selected from hydrogen, methyl, and ethyl.

In some embodiments, $R_7$ is selected from hydrogen and methyl. In some embodiments, $R_7$ is hydrogen.

The moieties $R_8$ and $R_9$ are independently selected from C1-C6 alkyl.

In some embodiments, $R_8$ and $R_9$ are independently selected from C1-C6 alkyl. When $R_8$ and $R_9$ are selected from C1-C6 alkyl, $R_8$ and $R_9$ for example may be selected from C1-C5 alkyl; or from C1-C4 alkyl; or from C1-C3 alkyl; e.g. from methyl and ethyl.

In some embodiments, when $R_8$ and $R_9$ are selected from C1-C6 alkyl, both $R_8$ and $R_9$ are ethyl.

In some embodiments, $R_1$ is C1-C6 alkyl; $R_2$ is hydrogen; $R_7$ is hydrogen; and $R_8$ and $R_9$ are independently selected from C1-C6 alkyl.

In some embodiments, $R_1$ a C1-C6 alkyl; $R_2$ is hydrogen; $R_7$ is hydrogen; and $R_8$ and $R_9$ are independently selected from C1-C6 alkyl. In some of these embodiments, $R_1$, $R_8$ and $R_9$ are independently selected from C1-C3 alkyl.

In some further embodiments, $R_1$ is C1-C3 alkyl; $R_2$, $R_4$, $R_5$ and $R_7$ are hydrogen; and $R_8$ and $R_9$ are independently selected from C1-C3 alkyl. In some of these embodiments, $R_1$ is selected from methyl, ethyl and iso-propyl; and $R_8$ and $R_9$ are the same or different and selected from methyl, ethyl and n-propyl. In some further embodiments, $R_1$ is selected from methyl, ethyl and iso-propyl; $R_2$, $R_4$, $R_5$, $R_6$, and $R_7$ are hydrogen; and $R_8$ and $R_9$ are the same or different and selected from methyl, ethyl and n-propyl.

In some embodiments, $R_2$ is selected from hydrogen and methyl; $R_3$, $R_4$, $R_5$, and $R_6$ are independently selected from hydrogen and chloro; $R_7$ is hydrogen; and $R_8$ and $R_9$ are the same or different and selected from methyl, ethyl and n-propyl.

In some embodiments, $R_1$ is selected from methyl, ethyl and iso-propyl; $R_2$ is hydrogen or methyl; $R_3$ is chloro or hydrogen; $R_4$, $R_5$, $R_6$, and $R_7$ are hydrogen; and $R_8$ and $R_9$ are the same or different and are selected from methyl, ethyl and n-propyl.

In some embodiments, $R_1$ is selected from methyl, ethyl and iso-propyl; $R_2$ is hydrogen or methyl; $R_3$ is chloro or hydrogen; $R_4$, $R_5$, $R_6$, and $R_7$ are hydrogen; and $R_8$ and $R_9$ are ethyl.

In some embodiments, $R_1$ is selected from methyl, ethyl and iso-propyl; $R_2$ is hydrogen; $R_3$ is chloro or hydrogen; $R_4$, $R_5$, $R_6$, and $R_7$ are hydrogen; and $R_8$ and $R_9$ are the same or different and are selected from methyl, ethyl and n-propyl.

In some embodiments, $R_1$ is selected from methyl, ethyl and iso-propyl; $R_2$ is hydrogen; $R_3$ is chloro; $R_4$, $R_5$, $R_6$, and $R_7$ are hydrogen; and $R_8$ and $R_9$ are the same or different and are selected from methyl, ethyl and n-propyl.

In some embodiments, the compound of formula (I) is selected from:
4-acetamido-3-chloro-N-[2-(diethylamino)ethyl]benzamide,
4-propanoylamino-3-chloro-N-[2-(diethylamino)ethyl]benzamide,
4-isobutyrylamino-3-chloro-N-[2-(diethylamino)ethyl]benzamide,
4-acetamido-N-[2-(diethylamino)ethyl]benzamide,
4-propanoylamino-N-[2-(diethylamino)ethyl]benzamide, and
4-isobutyrylamino-N-[2-(diethylamino)ethyl]benzamide.

In some embodiments, the compound of formula (I) is selected from:
4-acetamido-3-chloro-N-[2-(diethylamino)ethyl]benzamide,
4-propanoylamino-3-chloro-N-[2-(diethylamino)ethyl]benzamide,
4-isobutyrylamino-3-chloro-N-[2-(diethylamino)ethyl]benzamide, and
4-acetamido-N-[2-(diethylamino)ethyl]benzamide.

In some embodiments, the compound of formula (I) is selected from:
4-acetamido-3-chloro-N-[2-(diethylamino)ethyl]benzamide,
4-propanoylamino-3-chloro-N-[2-(diethylamino)ethyl]benzamide, and
4-isobutyrylamino-3-chloro-N-[2-(diethylamino)ethyl]benzamide.

In some further embodiments, a compound of formula (I) is selected from:
4-propanoylamino-3-chloro-N-[2-(diethylamino)ethyl]benzamide, and
4-isobutyrylamino-3-chloro-N-[2-(diethylamino)ethyl]benzamide.

In some embodiments, the compound of formula (I) is 4-acetamido-3-chloro-N-[2-(diethylamino)ethyl]benzamide.

In some embodiments, the compound of formula (I) is 4-propanoylamino-3-chloro-N-[2-(diethylamino)ethyl]benzamide.

In some embodiments, the compound of formula (I) is 4-isobutyrylamino-3-chloro-N-[2-(diethylamino)ethyl]benzamide.

In some embodiments, the compound of formula (I) is 4-acetamido-N-[2-(diethylamino)ethyl]benzamide.

In some embodiments, the compound of formula (I) is 4-propanoylamino-N-[2-(diethylamino)ethyl]benzamide.

In some embodiments, the compound of formula (I) is 4-isobutyrylamino-N-[2-(diethylamino)ethyl]benzamide.

In some embodiments, the pharmaceutically acceptable salt or solvate of the compound of formula (I) more particularly is a pharmaceutically acceptable salt of said compound, e.g. a hydrochloride, such as 4-acetamido-3-chloro-N-[2-(diethylamino)ethyl]benzamide hydrochloride.

Structural formulas of some compounds as mentioned herein are shown in Table 1.

TABLE 1

| | |
|---|---|
| 4-acetamido-3-chloro-N-[2-(diethylamino)ethyl]benzamide | 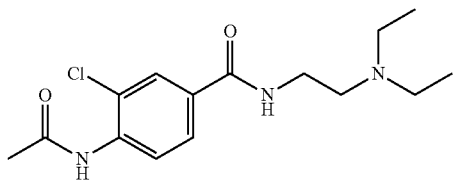 [SMILES: CCN(CC)CCNC(=O)c1ccc(NC(C)=O)c(Cl)c1] |
| 4-propanoylamino-3-chloro-N-[2-(diethylamino)ethyl]benzamide | 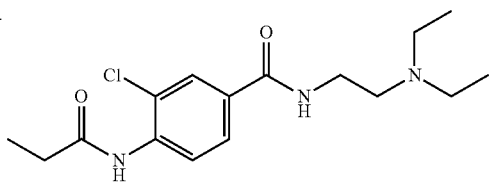 |
| 4-isobutyrylamino-3-chloro-N-[2-(diethylamino)ethyl]benzamide | 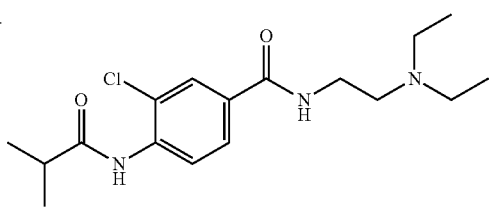 |
| 4-acetamido-N-[2-(diethylamino)ethyl]benzamide | 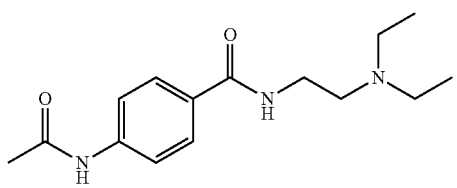 [SMILES: CCN(CC)CCNC(=O)c1ccc(NC(C)=O)cc1] |
| 4-propanoylamino-N-[2-(diethylamino)ethyl]benzamide | 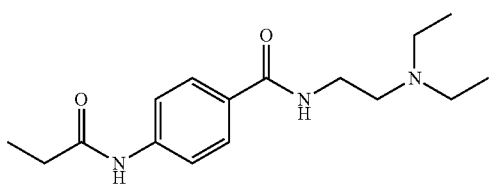 [SMILES: CCC(=O)Nc1ccc(C(=O)NCCN(CC)CC)cc1] |
| 4-isobutyrylamino-N-[2-(diethylamino)ethyl]benzamide | 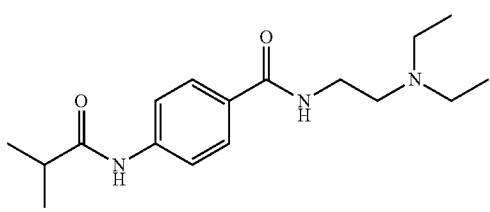 [SMILES: CCN(CC)CCNC(=O)c1ccc(NC(=O)C(C)C)cc1] |

The Pharmaceutically Acceptable Salts

The AABZ may be provided as a pharmaceutically acceptable salt of a compound of formula (I), e.g. an acid addition salt. In the preparation of acid or base addition salts, preferably such acids or bases are used which form suitably therapeutically acceptable salts. Examples of such acids are hydrohalogen acids, sulfuric acid, phosphoric acid, nitric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulfonic acid, ethanesulfonic acid, hydroxyethanesulfonic acid, halogenbenzenesulfonic acid, toluenesulfonic acid or naphthalenesulfonic acid. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Examples of bases useful in preparing salts of the present invention include sodium hydroxide, potassium hydroxide, ammonium hydroxide, potassium carbonate, and the like.

In some embodiments the compound of formula (I) is provided as a hydrochloride.

Relevant teachings relating to salt formulations as used herein and processes for preparing the same are described, e.g., in U.S. Pat. No. 3,177,252, and such teachings are hereby incorporated by reference into this application.

The Pharmaceutically Acceptable Solvate

Any pharmaceutically acceptable solvate is contemplated as possible according to the present invention. Exemplary solvates include, but are not limited to, hydrates, ethanolates, methanolates, and isopropanolates.

In some embodiments, the solvate is a hydrate.

Methods of Preparing the Compound of Formula (I)

The compounds of formula (I) may be prepared by the person of ordinary skill in the art, e.g. by following the general procedures of US Pat. Appl. No. 2011/0027179, and WO 2005/025498.

For example, a compound of formula (I) may be prepared by a method comprising two consecutive nucleophilic substitution reactions as represented by the following reaction scheme:

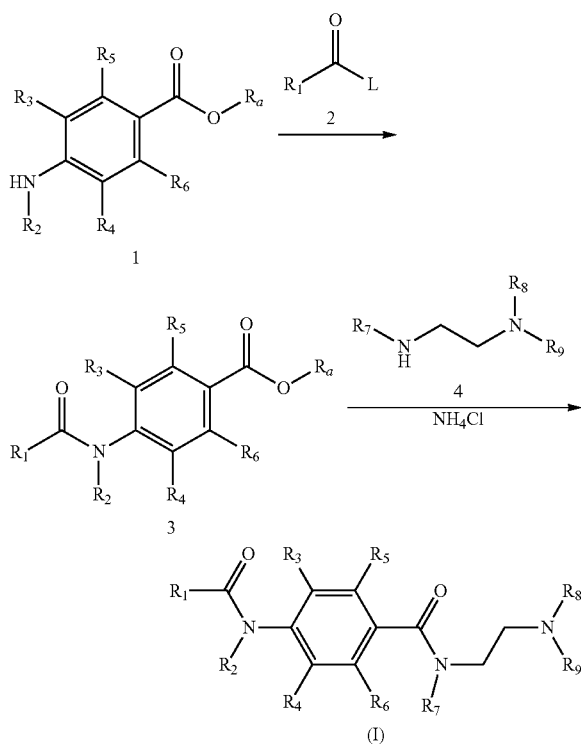

In the above reaction scheme, compound 1, where $R_a$ is e.g. C1-C3 alkyl, is reacted with compound 2, where L is a suitable leaving group, e.g. Cl, to obtain compound 3. Compound 3 is subsequently reacted with the secondary amine 4 in the presence of ammonium chloride as a catalyst for the reaction, to obtain the compound of formula (I) as defined herein. The compound of formula (I) may optionally be transformed to a suitable pharmaceutically acceptable salt or solvate, e.g. a hydrohalide salt.

The Use of the Compound of Formula (I)

The compound of formula (I) or the pharmaceutically acceptable salt or solvate thereof (collectively referred to herein below as AABZ) is useful for the treatment of a disease resulting from SpA.

In some embodiments, the disease resulting from SpA is a disease selected from axSpA, PsA and EnA.

In some embodiments, the disease resulting from SpA is a disease selected from axSpA and PsA.

In some embodiments, the disease resulting from SpA is a disease selected from axSpA and EnA.

In some embodiments, the disease resulting from SpA is a disease selected from PsA and EnA.

In some embodiments, the disease resulting from SpA is an axSpA.

In some embodiments, the disease resulting from SpA is PsA.

In some embodiments, the disease resulting from SpA is EnA.

Very advantageously, the AABZ may be used in the treatment of diseases resulting from SpA in a patient for which conventional treatment e.g. NSAID and DMRAD agents or therapeutics targeting such as TNF, IL-17A, or IL-12/23 are not considered useful, e.g. because the patient does not provide an adequate response to such treatment or because such treatment for some other reason is contraindicated. For example, the patient may be one suffering from a SpA for which anti-TNF-α treatment using TNF-α blockers does not provide adequate relief or cause adverse effects.

Symptoms of the disease resulting from SpA may range from mild to severe.

Signs and symptoms that are common to diseases resulting from SpA include pain and stiffness, and furthermore, bone formation and poor function.

One particularly advantageous embodiment is a method as defined herein, for the treatment of a patient suffering from a disease resulting from SpA, e.g. AS or PsA, for which NSAID, DMARD or anti-TNF-α treatment has failed or is contraindicated.

An advantageous feature of the AABZ is linked to its low affinity for the dopamine D2 receptor, which substantially reduces the risk for the development of adverse movement disorders such as short-term extrapyramidal disorders and tardive dyskinesia. One aspect therefore is an AABZ that may be used in long term treatment of a disease resulting from SpA without the negative effects of dopamine D2 receptor blockade.

In some embodiments, the AABZ used herein is a pharmaceutically acceptable salt of a compound of formula (I), in particular a hydrochloride salt.

In some embodiments, the AABZ is administered via oral administration.

In some embodiments, the AABZ is administered in a preferably solid unit formulation, which more preferably is a tablet.

In some embodiments, the AABZ is administered daily.

In some embodiments, the amount of the AABZ administered is 0.1-25 mg/kg (mg of drug per kg of body weight of subject) per day (any weight value being based on the non-salt, non-solvate form). In other embodiments, the administered amount of the AABZ is 0.3-10 mg/kg per day.

In some embodiments, the amount of the AABZ administered is 5.0-2000 mg/day, or 10-1000 mg/day.

In some embodiment, the AABZ is administered once daily. In other embodiments, the AABZ is administered twice daily. In other embodiments, the AABZ is administered three times daily. In yet other embodiments, the AABZ is administered four times daily.

In some embodiments, the administration of the AABZ continues for at least 2 weeks. In other embodiments, the administration of the AABZ continues for 3 months or more. In yet other embodiments, the administration of the AABZ continues for 12 months or more.

The Treated Subject

The subject that is treated according to the present invention is a mammal, including a human and a non-human mammal (an animal). Examples, of non-human mammals are primates, domesticated animals, e.g. farm animals, e.g. cattle, sheep, pigs, horses and the like, as well as pet animals, such as dogs and cats, and the like. In preferred embodiments, the subject is a human. In some other embodiments, the subject is a non-human mammal, e.g. a dog or a horse.

The Pharmaceutical Composition

One aspect is a pharmaceutical composition useful in treating a subject afflicted with a disease resulting from SpA, comprising an amount of an AABZ, and optionally (but preferably) at least one pharmaceutically acceptable excipient, such as a carrier.

In some embodiments, the pharmaceutical composition is for use in a method for the treatment of a subject afflicted with a disease selected from AS, PsA or enteropathic arthritis.

The AABZ can be administered in admixture with suitable pharmaceutical diluents, extenders, or carriers, or any other pharmaceutically acceptable excipients, suitably selected with respect to the intended form of administration and as consistent with conventional pharmaceutical practices. A preferred dosage unit will be in a form suitable for oral administration. The AABZ can be administered alone but is generally mixed with a pharmaceutically acceptable carrier, and administered in the form of a tablet or capsule, liposome, or as an agglomerated powder. Examples of suitable solid carriers include lactose, sucrose, gelatine and agar. Capsule or tablets can be easily formulated and can be made easy to swallow or chew; other solid forms include granules, and bulk powders.

Tablets may contain suitable binders, lubricants, disintegrating agents, colouring agents, flavouring agents, flow-inducing agents, and melting agents. For instance, for oral administration in the dosage unit form of a tablet or capsule, the AABZ can be combined with an oral, non-toxic, pharmaceutically acceptable, inert carrier such as lactose, gelatine, agar, starch, sucrose, glucose, methyl cellulose, dicalcium phosphate, calcium sulphate, mannitol, sorbitol, microcrystalline cellulose and the like. Suitable binders include starch, gelatine, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

The amount of AABZ in a dose unit of the formulation (e.g. a tablet or capsule) may be e.g. 5-500 mg (any amount is based on the compound of formula (I) in non-salt form and non-solvated form).

In some embodiments, the amount of AABZ is 10-100 mg. In other embodiments, the amount of AABZ is 5-25 mg. In one embodiment, the amount of AABZ in the composition is 500 mg. In other embodiments, the amount of AABZ is 25 mg. In other embodiments, the amount of AABZ is 100 mg. In other embodiments, the amount of AABZ is 10 mg. In other embodiments, the amount of AABZ is less than 10 mg.

In some embodiments the total amount of the AABZ is between 0.1 and 95% by weight of the formulation, e.g. between 0.5 and 50% by weight, or between 1 and 20% by weight, the remainder comprising e.g. a carrier and any other excipient.

In some embodiments, the pharmaceutical composition comprises 4-acetamido-3-chloro-N-[2-(diethylamino)ethyl] benzamide or pharmaceutically acceptable salt thereof, such as the hydrochloride salt.

Combined Use of an AABZ and a Further Therapeutically Active Ingredient

One aspect herein is a method for the treatment of a disease resulting from SpA, in a mammal for which NSAID, DMARD and anti-TNF-α treatment is not useful, comprising administering a combination of a compound of formula (I) as defined herein, or a pharmaceutically acceptable salt or solvate thereof (an AABZ), and at least one further therapeutically active ingredient, to a mammal in need of such treatment.

In some embodiments, the treatment comprises administering to a subject (a mammal, e.g. a human) an amount of an AABZ, and a further therapeutically active ingredient, wherein the amounts when taken together are therapeutically effective to treat the subject.

In some embodiments, the total amount of the AABZ and the further therapeutically active ingredient when administered together to treat a subject produces an overall better effect, i.e., a synergistic effect, than the simple sum of effects produced when either component, at the same total amount, is administered alone.

The further therapeutically active ingredient may be selected e.g. from NSAIDs, DMARDs corticosteroids, antibiotics, immunosuppressive drugs and antibodies.

In some embodiments, the treatment comprises administering to a subject (a mammal patient, e.g. a human patient) an AABZ as an add-on therapy or in combination with a further therapeutically active ingredient in treating a subject afflicted with AS or e.g. EnA.

In some embodiments, the further therapeutically active ingredient is administered via oral administration. In yet other embodiments, the further therapeutically active ingredient is administered via rectal administration.

In some embodiments, the further therapeutically active ingredient is administered once daily. In other embodiments, the further therapeutically active ingredient is administered twice daily. In other embodiments, the further therapeutically active ingredient is administered three times daily. In yet other embodiments, the further therapeutically active ingredient is administered four times daily.

The amount of the AABZ and the amount of the further therapeutically active ingredient when taken together preferably are effective to alleviate a symptom of a disease resulting from SpA, e.g. AS or EnA, in the subject.

In some embodiments, the administration of the further therapeutically active ingredient substantially precedes the administration of the AABZ, i.e. the subject is receiving therapy by administration of the further therapeutically active ingredient prior to initiating therapy by administration of the AABZ.

In some embodiments, the subject is receiving therapy by administration of the further therapeutically active ingredient for at least 6 months prior to initiating therapy by administration of the AABZ.

In some embodiments, the subject is receiving therapy by administration of the further therapeutically active ingredient for at least 12 months prior to initiating therapy by administration of the AABZ.

In some embodiments, the subject is receiving therapy by administration of the further therapeutically active ingredient for at least 24 months prior to initiating therapy by administration of the AABZ.

In some embodiments, the administration of the AABZ and the further therapeutically active ingredient continues for at least 2 weeks. In other embodiments, the administration of the AABZ and the further therapeutically active ingredient continues for 3 months or more. In yet other embodiments, the administration of the AABZ and the further therapeutically active ingredient continues for 12 months or more.

In some embodiments, the AABZ and the further therapeutically active ingredient are administered in combination with each other (simultaneously, or separately and concomitantly or sequentially) at the molar ratio of the AABZ to the further therapeutically active ranging from 1:100 to 100:1, from 1:50 to 50:1, from 1:20 to 20:1, from 1:10 to 10:1, from 1:5 to 5:1, or from 1:2 to 2:1, e.g. about 1:1.

In some embodiments, 4-acetamido-3-chloro-N-[2-(diethylamino)ethyl]benzamide or pharmaceutically acceptable salt thereof, such as the hydrochloride salt, and a further therapeutically ingredient are administered in combination with each other.

A further aspect is a method for the treatment of disease as mentioned herein, e.g. AS or enteropathic arthritis, by administering, to a mammal in need of such treatment, an AABZ as an add-on therapy or in combination with a further therapeutically active ingredient.

One aspect is a kit-of-parts comprising a combination of an AABZ and a further therapeutically active ingredient, wherein each one of components the AABZ and the further therapeutically active ingredient is optionally formulated in admixture with a pharmaceutically acceptable excipient, such as a carrier.

In some embodiments, a kit-of-parts is provided, comprising: a) a first pharmaceutical composition comprising an amount of an AABZ and a pharmaceutically acceptable carrier; b) a second pharmaceutical composition comprising an amount of a further therapeutically active ingredient and a pharmaceutically acceptable carrier; and c) instructions for use of the first and the second pharmaceutical compositions together; e.g. for use in the treatment of AS or enteropathic arthritis One aspect is a pharmaceutical composition comprising an amount of an AABZ, an amount of a further therapeutically active ingredient, and optionally at least one pharmaceutically acceptable excipient, such as a carrier.

In some embodiments, the pharmaceutical composition is for use in treating a subject afflicted with AS, PsA or EnA.

Generally, a suitable pharmaceutical composition is one as described herein above, in connection with a pharmaceutical formulation of an AABZ, but in addition to the AABZ, the composition also contains a further therapeutically active ingredient.

In some embodiments, the molar ratio of the AABZ to the further therapeutically active in the pharmaceutical composition ranges from 1:100 to 100:1, from 1:50 to 50:1, from 1:20 to 20:1, from 1:10 to 10:1, from 1:5 to 5:1, or from 1:2 to 2:1, e.g. it may be about 1:1.

In some embodiments the total amount of the AABZ and the further therapeutically active ingredient is between 0.1 and 95% by weight of the formulation, e.g. between 0.5 and 50% by weight, or between 1 and 20% by weight, the remainder comprising e.g. a carrier and any other excipient.

In some embodiments, the pharmaceutical composition comprises an AABZ as disclosed herein, e.g. 4-acetamido-3-chloro-N-[2-(diethylamino)ethyl]benzamide or pharmaceutically acceptable salt thereof, such as the hydrochloride salt, and a further therapeutically active ingredient, and optionally a pharmaceutically acceptable excipient.

Specific examples of the techniques, pharmaceutically acceptable carriers and excipients that may be used to formulate oral dosage forms of the present invention are described, e.g., in EP 1 720 531 B1. General techniques and compositions for making dosage forms useful in the present invention are described-in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985) (and subsequent editions); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds).; Modern Pharmaceutics Drugs and the Pharmaceutical Sciences, Vol. 40 (Gilbert S. Banker, Christopher T. Rhodes, Eds). These references in their entireties are hereby incorporated by reference into this application.

The following examples are intended to illustrate the invention without restricting the scope thereof.

EXAMPLES

Intermediary 1

Ethyl-4-acetamido-3-chlorobenzoate

Ethyl-4-amino-3-chlorobenzoate (2.0 g, 10 mmol) and 1.4 g of triethylamine were dissolved in 20 mL of dichloromethane. 0.9 g of acetyl chloride in 5 mL of dichloromethane was added drop-wise at 0° C. The reaction mixture was allowed to reach room temperature, stirred for 3 hours, washed with water, and dried. The solvents were evaporated to yield 2.0 g of the title product.

Example 1

4-Acetamido-3-chloro-N-[2-(diethylamino)ethyl] benzamide hydrochloride 1.5 g of ethyl-4-acetamido-3-chlorobenzoate (1.5 g, 6.2 mmol) was dissolved in 15 mL of N,N-diethylethylenediamine together with a catalytic amount of ammonium chloride. The reaction mixture was refluxed for 3 hours. Dichloromethane was added and washing 4 times with water removed excess diamine. Drying and evaporation of the solvents yielded the free base of the title compound. The residue was dissolved in ethanol-ether and acidified with ethanolic HCl. The solid that precipitated was collected giving the title compound (1.1 g, 3.1 mmol, 50% yield). 1H NMR (DMSO-d6): δ 1.23 (t, 6H), 2.15 (s, 3H), 3.17-3.23 (6H), 3.65 (q, 2H), 7.88 (d, 1H), 7.94 (s, 1H), 8.06 (s, 1H), 9.05 (t, 1H), 9.68 (s, 1H), 10.42 (s, 1H).

Example 2

4-Propanoylamino-3-chloro-N-[2-(diethylamino) ethyl]benzamide hydrochloride

4-Amino-N-[2-(diethylamino)ethyl]benzamide hydrochloride (0.5 g, 1.6 mmol), pyridine (5.0 mL), and propionic anhydride (5.0 mL) were stirred at 50° C. for 2.5 hours. Then the volatiles were removed using a rotary evaporator. Water (5 mL) was added and evaporated. The residue was freeze dried from water and gave the title compound (0.6 g, 100% yield, HPLC purity 98%). 1H NMR (400 MHz, Methanol-d4) δ 8.07 (d, J=8.6 Hz, 1H), 8.01 (d, J=2.0 Hz, 1H), 7.83 (dd, J=8.6, 2.0 Hz, 1H), 3.76 (t, J=6.2 Hz, 2H), 3.39 (t, J=6.2 Hz, 2H), 3.34 (q, J=7.3 Hz, 4H), 2.52 (q, J=7.6 Hz, 2H), 1.36 (t, J=7.3 Hz, 6H), 1.23 (t, J=7.6 Hz, 3H).

Example 3

4-Isobutyrylamino-3-chloro-N-[2-(diethylamino)ethyl]benzamide hydrochloride

The compound 4-isobutyrylamino-3-chloro-N-[2-(diethylamino)ethyl]benzamide hydrochloride was obtained in essentially the same manner, by use of isobutyric anhydride instead of propionic anhydride. Purity by HPLC 99%.

1H NMR (400 MHz, Methanol-d4) δ 8.01 (d, J=2.2 Hz, 1H), 8.00 (d, J=8.5 Hz, 1H), 7.83 (dd, J=8.5, 2.0 Hz, 1H), 3.76 (t, J=6.2 Hz, 2H), 3.39 (t, J=6.2 Hz, 2H), 3.34 (q, J=7.3 Hz, 4H), 2.80 (hept, J=6.8 Hz, 1H), 1.36 (t, J=7.3 Hz, 6H), 1.24 (d, J=6.9 Hz, 6H).

Example 4

4-Acetamido-N-[2-(diethylamino)ethyl]benzamide hydrochloride

A suspension of 4-amino-N-[2-(diethylamino)ethyl]benzamide hydrochloride (2.5 g, 9.1 mmol) was stirred in 20 mL of anhydrous pyridine. To the suspension was added 10 mL of acetic anhydride. The reaction was slightly exothermic. After 1 hour the precipitate was filtered off, washed with ethyl acetate, and dried to afford the title compound (2.83 g, 9.0 mmol, 99% yield). Purity by NMR 98%. 1H NMR (400 MHz, Methanol-d4) δ 7.84 (d, 2H), 7.68 (d, 2H), 3.74 (t, 2H), 3.37 (t, 2H), 3.35-3.29 (m, 4H), 2.14 (s, 3H), 1.35 (t, 6H).

Biological Assays

Macrophages serve a critical role in the initiation and propagation of inflammatory responses by releasing proinflammatory mediators, such as TNF-α. Lipopolysaccharide (LPS) is a potent initiator of an inflammatory response. During LPS stimulation, NF-κB signaling is activated to regulate the transcription of numerous genes involved in immunity and inflammation to produce proinflammatory cytokines, such as TNF-α. Suppression of LPS-induced TNF-α production in RAW264.7 macrophages treated with AABZ was investigated by evaluation of the generation of TNF-α.

Example 5

Suppression of LPS-Induced TNF-α Production in Macrophages Treated with AABZ

The RAW264.7 macrophage line was maintained in DMEM supplemented with 5% FBS at 37° C. in a 5% CO2-humidified air environment. The RAW264.7 cells were seeded in 96-well plates at a density of 1×105/ml and a volume of 200 μl/well. The cells were incubated for 24 h in medium supplemented with 10% FBS and were then preincubated with or without the indicated concentrations of test substances for 2 h prior to the addition of LPS (1 μg/ml). The supernatants were subsequently harvested at various time points and production of the proinflammatory cytokine TNF-α in the culture medium was determined using a commercially available enzyme-linked immunosorbent assay (ELISA) kit according to the manufacturer's protocol.

Effects of some AABZs of the invention at 1 mM on LPS-induced TNF-production in RAW264.7 murine macrophage cells are shown in Table 2.

TABLE 2

Effects of AABZs at 1 mM on LPS-induced TNF-production in RAW264.7 murine macrophage cells

| Compound | % Inhibition of TNF-production |
| --- | --- |
| LPS-treated control | 0 |
| 4-Acetamido-3-chloro-N-[2-(diethylamino)ethyl]benzamide hydrochloride* | 45 |
| 4-Propanoylamino-3-chloro-N-[2-(diethylamino)ethyl]benzamide hydrochloride | 50 |
| 4-Isobutyrylamino-3-chloro-N-[2-(diethylamino)ethyl]benzamide hydrochloride | 63 |
| 4-Acetamido-N-[2-(diethylamino)ethyl]benzamide hydrochloride | 56 |

*Cpd A

It was observed that different concentrations (0.3, 1.0, and 3.0 mM) of the compounds significantly reduced the expression levels of TNF in comparison with the LPS-treated control group. These results support the usefulness of compounds as disclosed herein, for the treatment of diseases resulting from SpA.

Example 6

Assessment of Efficacy of AABZ in Collagen-Induced Arthritis

The experiment was performed using 9-week old male DBA/1 mice after a two-week acclimatization period. The mice were purchased from B&M (Denmark), and were maintained in a temperature and light-controlled facility with free access to standard rodent chow and water. Following the acclimatization period, the mice (10 per treatment group) were anesthetized with Enflurane and immunized intradermally in the base of the tail with 100 mL of a 1:1 emulsion consisting of Freund's Complete Adjuvant H37Ra (Difco) and 2 mg/mL bovine type II collagen (Elastin Products, Owensville, Mo.) in 0.1 M acetic acid. On day 14 post-immunization, the mice were given ad lib access to drinking water containing Cpd A, with treatment continuing daily until termination of the experiment (day 49). The Cpd A intake was monitored by weighing the drinking bottles at the water renewal twice per week. The control group received water ad lib.

The mice were monitored for clinical signs of arthritis three times a week from immunization to day 49. The scoring system (arthritis score) was employed as follows: 0=no arthritis; 1=arthritis (erythema or swelling) in one of either interphalangeal, metatarsophalangeal or intercarpal/wrist joints; 2=arthritis in two of the above joints; 3=arthritis in three of the above joints; 4=arthritis in three of the above joints and the mouse does not support on the paw. The four measurements were summed for each mouse, and group averages were calculated. Mice with a score>12 were sacrificed. In the scoring protocol, the last observation carried forward (LOCF) method was used. Mean onset day was defined as the mean day of onset in mice being affected. Mean arthritis clinical score was defined as the mean score of an experimental group from day 14 until termination of the experiment.

Statistical significance was determined using Mann-Whitney Rank Sum test. Treatment with Cpd A resulted in a statistically significant delayed onset of disease and an amelioration of disease severity. In the mice receiving a dosage of 200 mg/kg/day of Cpd A, the mean onset of disease was delayed by 5.8 days (p=0.02) compared to the control group, and the severity of arthritis score was reduced by 1.6 (p=0.05).

Example 7

Receptor Affinity

It is well-known that drug compounds that have an affinity for the striatal dopamine D2 may give rise to adverse side effects, such as short-term extrapyramidal disorders and tardive dyskinesia. Such adverse effects e.g. have been observed for metoclopramide (CAS No.: 364-62-5), which reduces its utility in particular for the long term treatment of chronic diseases. The in vitro affinity for the dopamine D2 receptor of Cpd A, and of two prior art compounds metoclopramide and declopramide (CAS No.: 891-60-1) was investigated using an in vitro radioligand binding technique with $125_I$-spiperone as the radioactive ligand. As shown in Table 3, Cpd A displays a very low affinity for the dopamine D2 subtype receptor.

TABLE 3

Dopamine D2 receptor affinity.

| Compound | IC50 (µM) |
|---|---|
| Metoclopramide | 0.07 |
| Declopramide | 38.6 |
| Cpd A | 975 |

REFERENCES

Liberg D et al., Br J Cancer. 1999 81:981-8.
Lindgren H et al., Mol Immunol. 2001 38:267-77.
Lindgren H et al., Biochem Biophys Res Commun. 2003 301:204-11.
Thompson J E et al., Cell. 1995 80:573-82.

The invention claimed is:

1. A method for the treatment a disease resulting from spondyloarthritis by administering, to a mammal in need of such treatment, a therapeutically effective amount of a compound of formula (I)

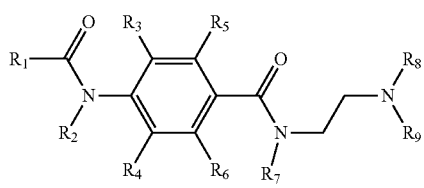

(I)

or a pharmaceutically acceptable salt or solvate thereof; wherein
$R_1$ is selected from C1-C6 alkyl and C3-C6 cycloalkyl;
$R_2$ is selected from hydrogen and C1-C3 alkyl;
$R_3$, $R_4$, $R_5$, and $R_6$ are independently selected from hydrogen, C1-C3 alkyl, C1-C3 alkoxy, C1-C3 alkylthio, fluoro, chloro, and bromo, wherein any alkyl is optionally substituted with one or more fluoro;
$R_7$ is selected from hydrogen and C1-C3 alkyl;
$R_8$ and $R_9$ are independently selected from C1-C6 alkyl.

2. The method according to claim 1, wherein
$R_3$, $R_4$, $R_5$, and $R_6$ are independently selected from hydrogen, C1-C2 alkyl, C1-C2 alkoxy, C1-C2 alkylthio, fluoro, chloro, bromo, and trifluoromethyl;
$R_7$ is selected from hydrogen and C1-C3 alkyl; and
$R_8$ and $R_9$ are independently selected from C1-C6 alkyl.

3. The method according to claim 1, wherein
$R_1$ is selected from C1-C3 alkyl;
each one of $R_2$, $R_4$, $R_5$, $R_6$ and $R_7$ is hydrogen; and
$R_8$ and $R_9$ are independently selected from C1-C4 alkyl.

4. The method according to claim 1, wherein the compound is selected from:
4-acetamido-3-chloro-N-[2-(diethylamino)ethyl]benzamide,
4-propanoylamino-3-chloro-N-[2-(diethylamino)ethyl]benzamide,
4-isobutyrylamino-3-chloro-N-[2-(diethylamino)ethyl]benzamide,
4-acetamido-N-[2-(diethylamino)ethyl]benzamide,
4-propanoylamino-N-[2-(diethylamino)ethyl]benzamide, and
4-isobutyrylamino-N-[2-(diethylamino)ethyl]benzamide.

5. The method according to claim 4, wherein the compound is selected from:
4-acetamido-3-chloro-N-[2-(diethylamino)ethyl]benzamide,
4-propanoylamino-3-chloro-N-[2-(diethylamino)ethyl]benzamide,
4-isobutyrylamino-3-chloro-N-[2-(diethylamino)ethyl]benzamide, and
4-acetamido-N-[2-(diethylamino)ethyl]benzamide.

6. The method according to claim 4, wherein the compound is 4-acetamido-3-chloro-N-[2-(diethylamino)ethyl]benzamide.

7. The method according to claim 4, wherein the compound is 4-propanoylamino-3-chloro-N-[2-(diethylamino)ethyl]benzamide.

8. The method according to claim 4, wherein the compound is 4-isobutyrylamino-3-chloro-N-[2-(diethylamino)ethyl]benzamide.

9. The method according to claim 4, wherein the compound is 4-acetamido-N-[2-(diethylamino)ethyl]benzamide.

10. The method according to claim 1, wherein the disease is selected from axial spondyloarthritis, psoriatic arthritis and enteropathic arthritis.

11. The method according to claim 10, wherein the disease is selected from axial spondyloarthritis and psoriatic arthritis.

12. The method according to claim 10, wherein the disease is selected from axial spondyloarthritis and enteropathic arthritis.

13. The method according to claim 10, wherein the disease is axial spondyloarthritis.

14. The method according to claim 4, wherein the disease is selected from axial spondyloarthritis, psoriatic arthritis and enteropathic arthritis.

15. The method according to claim 14, wherein the disease is selected from axial spondyloarthritis, and psoriatic arthritis.

16. The method according to claim 14, wherein the disease is selected from axial spondyloarthritis, and enteropathic arthritis.

17. The method according to claim 14, wherein the disease is axial spondyloarthritis.

* * * * *